(12) United States Patent
Hall et al.

(10) Patent No.: US 11,484,252 B2
(45) Date of Patent: Nov. 1, 2022

(54) DEVICE FOR PROVIDING HEALTH AND WELLNESS DATA THROUGH FOOT IMAGING

(71) Applicant: Hall Labs LLC, Provo, UT (US)

(72) Inventors: David R. Hall, Provo, UT (US); David Crismon, Herriman, UT (US); Joshua Larsen, Spanish Fork, UT (US); Jared Reynolds, Spanish Fork, UT (US); Michael Brough, Provo, UT (US)

(73) Assignee: Medic, Inc., Provo, UT (US)

( * ) Notice: Subject to any disclaimer, the term of this patent is extended or adjusted under 35 U.S.C. 154(b) by 433 days.

(21) Appl. No.: 16/578,118

(22) Filed: Sep. 20, 2019

(65) Prior Publication Data

US 2020/0390384 A1 Dec. 17, 2020

Related U.S. Application Data

(60) Provisional application No. 62/862,284, filed on Jun. 17, 2019, provisional application No. 62/862,603, filed on Jun. 17, 2019, provisional application No. 62/862,278, filed on Jun. 17, 2019.

(51) Int. Cl.
*A61B 5/00* (2006.01)
*G06T 7/00* (2017.01)
*A47K 17/02* (2006.01)
*A61B 8/08* (2006.01)
*A61B 5/01* (2006.01)

(52) U.S. Cl.
CPC ............ *A61B 5/4538* (2013.01); *A47K 17/02* (2013.01); *A61B 5/0077* (2013.01); *A61B 5/015* (2013.01); *A61B 5/6887* (2013.01); *A61B 8/483* (2013.01); *G06T 7/0016* (2013.01); *G06T 7/97* (2017.01); *G06T 2207/30004* (2013.01)

(58) Field of Classification Search
CPC ..................... G06T 7/0016; G06T 7/97; G06T 2207/10048; G06T 2207/30004; G06T 2207/10028; G06T 2207/10024; G06T 2207/30088; A61B 5/015; A61B 8/483; A61B 5/6887; A61B 5/4538; A47K 17/02
See application file for complete search history.

(56) References Cited

U.S. PATENT DOCUMENTS

| | | | |
|---|---|---|---|
| 9,615,746 B2 * | 4/2017 | Horseman | ................ A61B 5/01 |
| 9,756,297 B1 * | 9/2017 | Clements | ............... A61B 5/444 |
| 9,949,640 B2 * | 4/2018 | Horseman | ............ A61B 5/0537 |

(Continued)

*Primary Examiner* — Brenda C Bernardi

(57) ABSTRACT

A system to provide health and wellness data, comprising a platform for placement; at least one imaging sensor associated with the platform for capturing images; and a processor adapted to analyze the images to determine health and wellness data is disclosed. A toilet for assessing health and wellness of a user, comprising a bowl supported by a base; a platform for placement of a user's feet; at least one imaging sensor mounted on the base; and a processor adapted to analyze the images to determine health and wellness is disclosed. A method for assessing health and wellness comprising acquiring one or more images of the foot a user; using a processor to analyze the one or more images for health and wellness factors; and making the results of the health and wellness analysis available to the user on one or more digital platforms is disclosed.

18 Claims, 15 Drawing Sheets

(56) References Cited

U.S. PATENT DOCUMENTS

| | | | |
|---|---|---|---|
| 2013/0261495 A1* | 10/2013 | Linders | A61B 5/6807 600/549 |
| 2016/0256056 A1* | 9/2016 | Petersen | G16H 50/20 |
| 2018/0087969 A1* | 3/2018 | Hall | E03D 11/13 |
| 2019/0021649 A1* | 1/2019 | Van Snellenberg | A61B 5/0035 |
| 2019/0272727 A1* | 9/2019 | Yang | G08B 21/043 |

* cited by examiner

DEVICE FOR PROVIDING HEALTH AND WELLNESS DATA THROUGH FOOT IMAGING

CROSS-REFERENCE TO RELATED APPLICATIONS

This application claims priority to U.S. Provisional Application No. 62/862,278 filed on Jun. 17, 2019; 62/862,284 filed on Jun. 17, 2019; and U.S. 62/862,603 filed on Jun. 17, 2019, which are all incorporated herein by reference in their entireties.

TECHNICAL FIELD

The present disclosure relates to the field of devices useful in assessing health and wellness. More particularly, it relates to the use of imaging technology on legs and feet to assess health and wellness.

BACKGROUND

The ability to track an individual's health and wellness is currently limited to the lack of available data related to personal health. Digital long wave infrared (LWIR) imaging, thermal imaging, near infrared (NIR) imaging, visual imaging, and 3D imaging, have the capacity to uncover important health indicators and trends related to many conditions. While these or other diagnostic tools are available for these conditions, the high cost of frequent doctor's visits and/or scans make these options available only on a very limited and infrequent basis. Thus, they are not widely available to people interested in tracking their own personal wellbeing. Foot and ankle health, particularly inflammation and temperature, which can be measured with infrared sensors, can provide valuable information that would otherwise be unavailable.

Toilets present a fertile environment for locating a variety of useful sensors to detect, analyze, and track trends for multiple health conditions. Locating sensors in such a location allows for passive observation and tracking on a regular basis of daily visits without the necessity of visiting a medical clinic for collection of samples and data. Monitoring trends over time of health conditions supports continual wellness monitoring and maintenance rather than waiting for symptoms to appear and become severe enough to motivate a person to seek care. At that point, preventative care may be eliminated as an option leaving only more intrusive and potentially less effective curative treatments. An ounce of prevention is worth a pound of cure.

Leg and foot health are affected by multiple conditions, including many originating in or affecting other parts of the body. Therefore, monitoring trends in leg and foot health is an effective method of achieving overall wellness care. The following is a non-exclusive list of some of the conditions that may be detected by imaging the feet.

A diabetic foot ulcer is an open sore or wound that occurs in approximately 15 percent of patients with diabetes and is commonly located on the bottom of the foot. Of those who develop a foot ulcer, 6 percent will be hospitalized due to infection or other ulcer-related complications. Diabetes is the leading cause of non-traumatic lower extremity amputations in the United States, and approximately 14-24 percent of patients with diabetes who develop a foot ulcer will require an amputation. Foot ulceration precedes 85 percent of diabetes-related amputations. Research has shown, however, that development of a foot ulcer is preventable.

A bunion is a painful bony bump that develops on the inside of the foot at the big toe joint. Bunions are often referred to as hallux valgus. Bunions develop slowly. Pressure on the big toe joint causes the big toe to lean toward the second toe. Over time, the normal structure of the bone changes, resulting in the bunion bump. This deformity will gradually increase and may make it painful to wear shoes or walk.

Ingrown toenails are a common condition in which the corner or side of a toenail grows into the soft flesh. The result is pain, redness, swelling and, sometimes, an infection. Ingrown toenails usually affect the big toe.

Plantar fasciitis is one of the most common causes of heel pain. It involves inflammation of a thick band of tissue that runs across the bottom of your foot and connects your heel bone to your toes (plantar fascia). Plantar fasciitis commonly causes stabbing pain that usually occurs with your first steps in the morning. As you get up and move more, the pain normally decreases, but it might return after long periods of standing or after rising from sitting.

Hammertoe and mallet toe are foot deformities that occur due to an imbalance in the muscles, tendons or ligaments that normally hold the toe straight. The type of shoes you wear, foot structure, trauma and certain disease processes can contribute to the development of these deformities. A hammertoe has an abnormal bend in the middle joint of a toe. Mallet toe affects the joint nearest the toenail. Hammertoe and mallet toe usually occur in your second, third and fourth toes.

Athlete's foot (tinea pedis) is a fungal infection that usually begins between the toes. It commonly occurs in people whose feet have become very sweaty while confined within tightfitting shoes. Signs and symptoms of athlete's foot include a scaly rash that usually causes itching, stinging and burning. Athlete's foot is contagious and can be spread via contaminated floors, towels or clothing.

Gout is an illness that tends to affect the joints. It is accompanied by rather obvious pain and swelling and generally results from the presence of purine. Purine is found in a number of meats and contributes to high levels of uric acid, which in turn leads to gout when too much uric acid begins to stockpile in the joints and damage the body.

Thin, reddish-brown lines under the toenails are generally splinter hemorrhages. The appearance of splinter hemorrhages is not always an indicator of a serious problem, because they can, in fact, appear if the nails have been injured, but sometimes they are. Splinter hemorrhages are potentially the result of damaged blood vessels, generally from clots, and can reveal serious problems with the heart. Specifically, they can indicate endocarditis, which is an infection of the heart's lining; generally, endocarditis results from other heart conditions, or other heart-related issues.

Clubbed digits start out thin and then balloon into large spherical shapes. While this condition can appear somewhat comical, it could also reveal the presence of a serious illness, namely lung cancer or other lung problems. Problems with the lungs affect the digits because when the lungs are unwell, vascular resistance is decreased, which leads to a massive increase in blood flow to the extremities. this results in the swelling of tissue.

Irregular depressions or discoloration in the toenails may be a sign of psoriasis. Psoriasis may affect the skin or the nails although it affects the skin primarily. But it is possible to have a nail specific infection. Patches of white on your nails may be another indication. This is also true if your nails become tender and painful.

Koilonychia causes spoon-like depressions in the toenails. Koilonychia describes a nail that is concave, such that the entire nail is rounded and bent upward, much like a spoon. The most common cause for the formation of such nails is iron deficiency. However, there are other causes as well, including a surplus of iron in the body, as well as lupus.

Melanoma is a type of skin cancer that can be characterized by a long dark streak under the nail stretching from the base to the very tip. Generally, it will be both longer and thicker than splinter hemorrhage lines, and will be solitary, as compared to numerous thinner, shorter lines of splinter hemorrhages. While melanoma is relatively rare, it is the most serious form of skin cancer, tends to affect people of color more, and warrants seeking immediate treatment.

An increase in the height of foot arches may be the result of nerve damage. One possibility is a neurological condition known as Charcot-Marie-Tooth (CMT). It's a hereditary disorder that can result in damage to the peripheral nerves. Since the nerves connect to every part of the body, this can lead to problems in the feet, including numbness, muscle loss, and trouble with balance. These problems tend not to be limited to just the feet, however. Victims of CMT have been known to eventually experience similar issues in their arms and hands as well.

You have flatfeet when the arches on the inside of your feet are flattened, allowing the entire soles of your feet to touch the floor when you stand up. A common and usually painless condition, flatfeet can occur when the arches don't develop during childhood. In other cases, flatfeet develop after an injury or from the simple wear-and-tear stresses of age. If pain develops, custom orthotics may be needed.

Computer Vision ("CV") is a field of artificial intelligence that involves computers learning to view, interpret, and understand the visual world. It uses images from digital cameras and learning algorithms, computers use image processing to view multiple images and learn how to accurately recognize, identify, and classify object. CV is used in a variety of fields to identify things such as manufacturing defects, counterfeit currency, and early signs of disease in plants. Computer vision can be used to extract information from digital images to make decisions and take actions.

The use of imaging and temperature sensors to examine feet for health and wellness indicators is documented in the scientific literature. Examples include: *Infrared Thermal Imaging for Automated Detection of Diabetic Foot Complications*, Jaap J. van Netten et al., J. DIABETES SCI. TECHNOL., September 2013, 7(5): 1122-1129; *Using Noncontact Infrared Thermography for Long-term Monitoring of Foot Temperatures in a Patient with Diabetes Mellitus*, Erik Staffa et al., OSTOMY WOUND MANAGE., 2016; 62(4):54-61; *Correlation between Plantar Foot Temperature and Diabetic Neuropathy: A Case Study by Using an Infrared Thermal Imaging Technique*, Subramnaiam Bagavathiappan et al., J DIABETES SCI TECHNOL., 2010 November; 4(6): 1386-1392; and *An exploration of the relationship between foot skin temperature and blood flow in type 2 diabetes mellitus patients: a cross-sectional study*, Uraiwan Chatchawan et al., J PHYS THER SCI., 2018 November; 30(11): 1359-1363; *Diabetic Wound Imaging Using a Noncontact Near-Infrared Scanner*; Anuradha Godavarty et al., J DIABETES SCI TECHNOL., 2015 September; 9(5): 1158-1159; *Critical Review of Noninvasive Optical Technologies for Wound Imaging Critical Review of Noninvasive Optical Technologies for Wound Imaging*, Maanasa Jayachandran et al., ADV WOUND CARE (New Rochelle), 2016 Aug. 1; 5(8): 349-359; *Towards Commoditised Near Infrared Spectroscopy*, Simon Klakegg et al., available at www.nielsvanberkel.com/files/publications/dis17a.pdf; *Three-dimensional Imaging and Scanning: Current and Future Applications for Pathology*, Navid Farahani et al., J PATHOL INFORM., 2017; 8: 36. These publications are incorporated herein by reference in their entireties.

Just a few examples of smart toilets and other bathroom devices can be seen in the following U.S. patents and Published applications: U.S. Pat. No. 9,867,513, entitled "MEDICAL TOILET WITH USER AUTHENTICATION"; U.S. Pat. No. 10,123,784, entitled "IN SITU SPECIMEN COLLECTION RECEPTACLE IN A TOILET AND BEING IN COMMUNICATION WITH A SPECTRAL ANALYZER"; U.S. Pat. No. 10,273,674, entitled "TOILET BOWL FOR SEPARATING FECAL MATTER AND URINE FOR COLLECTION AND ANALYSIS"; US 2016/0000378, entitled "HUMAN HEALTH PROPERTY MONITORING SYSTEM"; US 2018/0020984, entitled "METHOD OF MONITORING HEALTH WHILE USING A TOILET"; US 2018/0055488, entitled "TOILET VOLATILE ORGANIC COMPOUND ANALYSIS SYSTEM FOR URINE"; US 2018/0078191, entitled "MEDICAL TOILET FOR COLLECTING AND ANALYZING MULTIPLE METRICS"; US 2018/0140284, entitled "MEDICAL TOILET WITH USER CUSTOMIZED HEALTH METRIC VALIDATION SYSTEM"; US 2018/0165417, entitled "BATHROOM TELEMEDICINE STATION"; U.S. Ser. No. 15/222,267, entitled "THIN WEIGHT SCALE." The disclosures of all of these patents and applications are incorporated by reference in their entireties.

SUMMARY

In a first aspect, the disclosure provides a system to provide health and wellness data to a user, comprising a platform for placement of a user's feet; at least one imaging sensor associated with the platform for capturing images of the user's feet; and a processor adapted to analyze the images to determine health and wellness data provided to the user.

In a second aspect, the disclosure provides a toilet for assessing health and wellness of a user, comprising a bowl supported by a base; a platform for placement of a user's feet; at least one imaging sensor mounted on the base for capturing images of the user's feet; and a processor adapted to analyze the images to determine health and wellness data for the user.

In a third aspect, the disclosure provides a method for assessing health and wellness comprising acquiring one or more images of the foot of a user; using a processor to analyze the one or more images for health and wellness factors; and making the results of the health and wellness analysis available to the user on one or more digital platforms.

Further aspects and embodiments are provided in the foregoing drawings, detailed description and claims.

BRIEF DESCRIPTION OF THE DRAWINGS

The following drawings are provided to illustrate certain embodiments described herein. The drawings are merely illustrative and are not intended to limit the scope of claimed inventions and are not intended to show every potential feature or embodiment of the claimed inventions. The drawings are not necessarily drawn to scale; in some instances, certain elements of the drawing may be enlarged with respect to other elements of the drawing for purposes of illustration.

DETAILED DESCRIPTION

Figure 1:
FIG. 1 is a perspective view of an exemplary embodiment of a health and wellness monitoring device according to the present disclosure.

The following description recites various aspects and embodiments of the inventions disclosed herein. No particular embodiment is intended to define the scope of the invention. Rather, the embodiments provide non-limiting examples of various compositions, and methods that are included within the scope of the claimed inventions. The description is to be read from the perspective of one of ordinary skill in the art. Therefore, information that is well known to the ordinarily skilled artisan is not necessarily included.

Definitions

The following terms and phrases have the meanings indicated below, unless otherwise provided herein. This disclosure may employ other terms and phrases not expressly defined herein. Such other terms and phrases shall have the meanings that they would possess within the context of this disclosure to those of ordinary skill in the art. In some instances, a term or phrase may be defined in the singular or plural. In such instances, it is understood that any term in the singular may include its plural counterpart and vice versa, unless expressly indicated to the contrary.

As used herein, the singular forms "a," "an," and "the" include plural referents unless the context clearly dictates otherwise. For example, reference to "a substituent" encompasses a single substituent as well as two or more substituents, and the like.

As used herein, "for example," "for instance," "such as," or "including" are meant to introduce examples that further clarify more general subject matter. Unless otherwise expressly indicated, such examples are provided only as an aid for understanding embodiments illustrated in the present disclosure and are not meant to be limiting in any fashion. Nor do these phrases indicate any kind of preference for the disclosed embodiment.

As used herein, "front," "back," and "side" are used to describe the disclosed system and devices from the perspective of a user. In the present disclosure, the user is assumed to be seated unless otherwise shown or stated to be standing facing the toilet.

As used herein, the terms "foot" and "feet" are intended to have a relatively broad meaning and used to reference the foot, ankle, and, in some cases, the calf area (i.e., leg below the knee) of the user.

As used herein, the term "bowl" refers to the portion of a toilet that is designed to receive excreta.

As used herein, the term "base" refers to the portion of the toilet below and around the bowl supporting it.

As used herein, the term "processor" refers to logic circuitry that processes data from the imaging sensors, applies algorithms such as computer vision to analyze the images for health and wellness indicators, and provide the resulting data to users. The processor may also be used to perform other tasks such as analyzing image data to determine the identity of a user.

As used herein, the term "sensor array" is used to describe the combination of two or more sensors of one or more types in a scanning device.

Exemplary Embodiments

The present disclosure relates to a system or device that uses imaging sensors, such as but not limited to visual, infrared, thermal, near infrared, and 3D cameras, to monitor foot health and wellness. In preferred embodiments, the imaging sensors are integrated with bathroom products such as a toilet or scale to integrate the disclosed devices with other health monitoring devices to consolidate health and wellness data collection into fewer user actions.

Referring to FIG. 1, a smart toilet including a platform 100 for placement of a user's feet is shown. In various embodiments, imaging sensors may be located at one or more positions around the user's feet. For example, imaging sensors may be placed under the user's feet; to the sides of the user's feet; above and to the front, back or sides of the user's feet; or behind the user's feet. In various other embodiments, the platform 100 may be part of another device, such as a bathroom scale, or may be an area of floor (e.g., in front of a toilet) where one or more sensors are focused. In various exemplary embodiments, the platform 100 may be a part of the floor itself, or a separate unit built into or placed on top of the floor and may include imaging sensors under the portion of the floor comprising the platform 100.

In FIG. 1, the user's feet are shown facing the toilet. In various exemplary embodiments, the system is capable of scanning feet regardless of how they are placed on the platform. In various exemplary embodiments, the system is capable of analyzing the image data to determine the orientation of the user's feet and adapt accordingly. However, in most embodiments the imaging sensor arrays are optimized for feet in one or two general positions, typically facing toward or away from a smart toilet.

In the embodiment of FIG. 1, the two imaging sensor arrays 110 are located behind the feet of a standing user or the front of the feet of a sitting user. In various other exemplary embodiments, sensor arrays 110 may be placed on or more other sides or in the interior of the platform 100. In addition to imaging, the sensor arrays 110 may be used to indicate the presence of a user to the toilet system.

Figure 2:
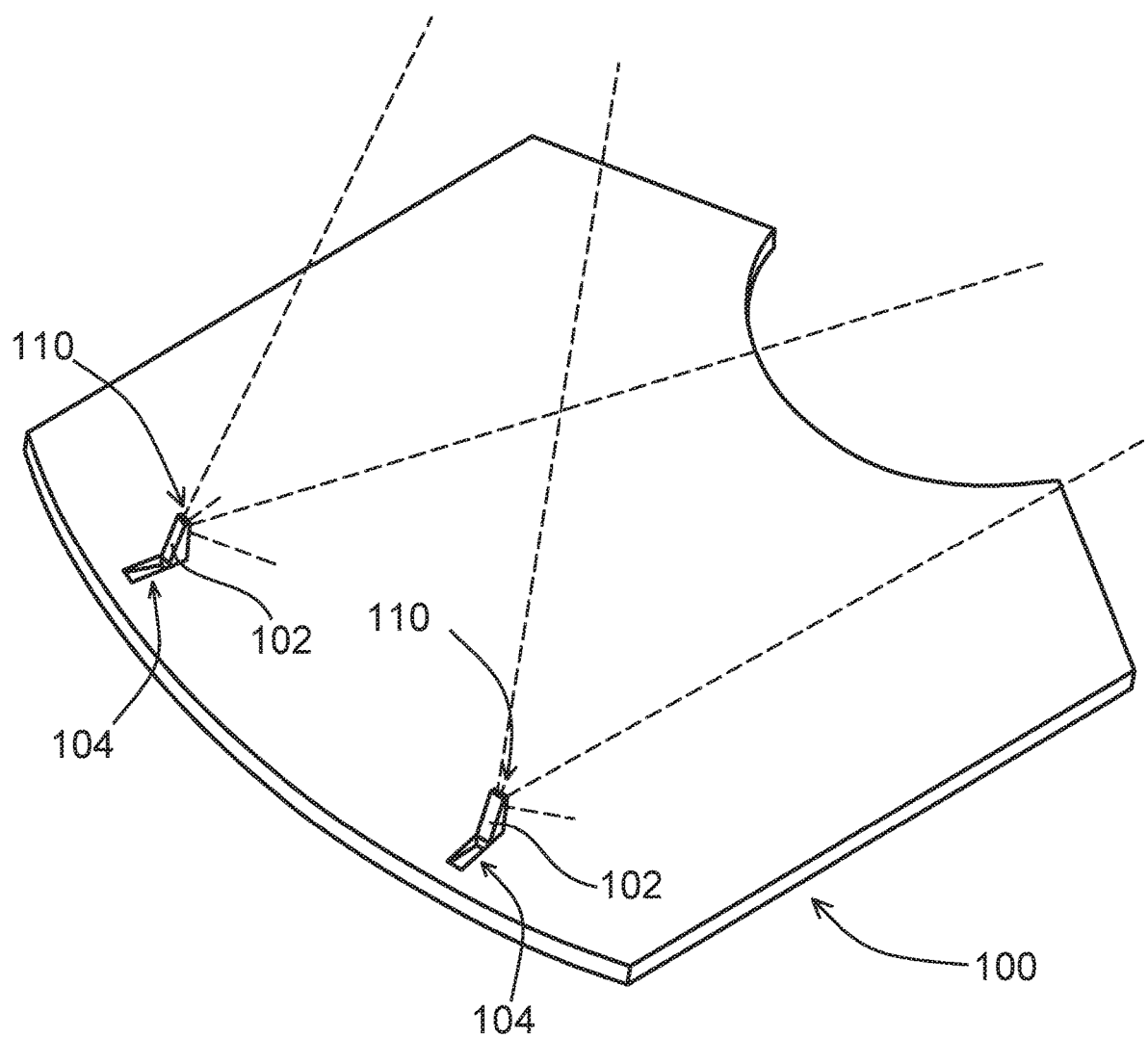
FIG. 2 is a perspective view of a first exemplary embodiment of a scanning device according to the present disclosure.
Figure 3:
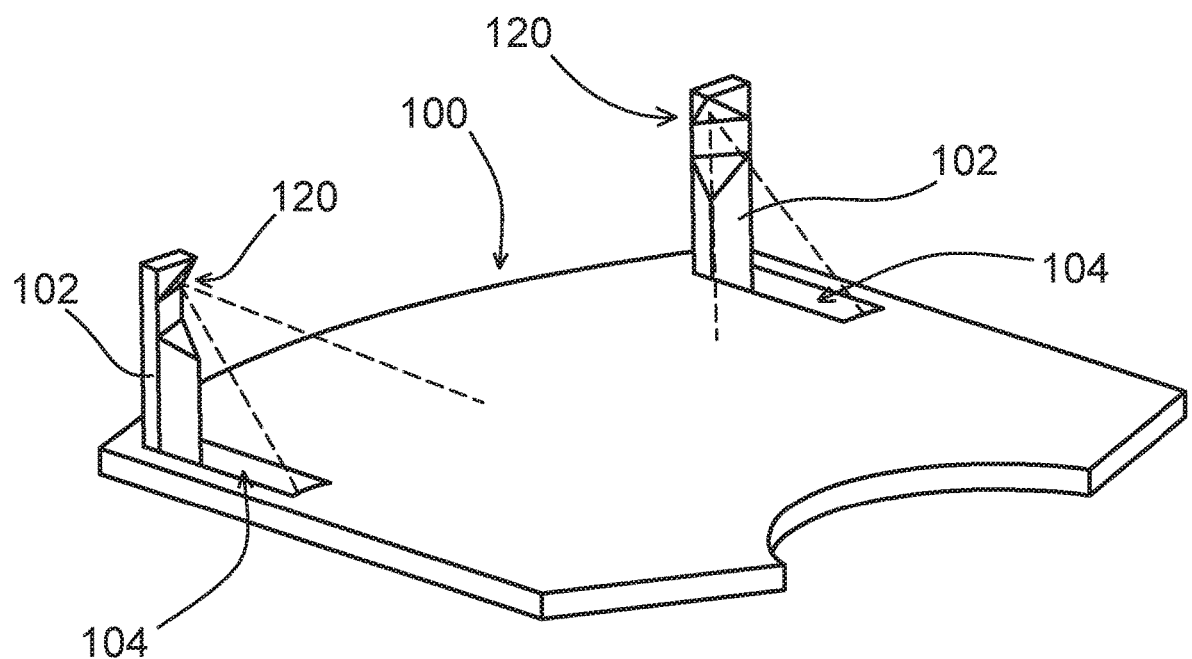
FIG. 3 is a perspective view of a second exemplary embodiment of a scanning device according to the present disclosure.
Figure 4:
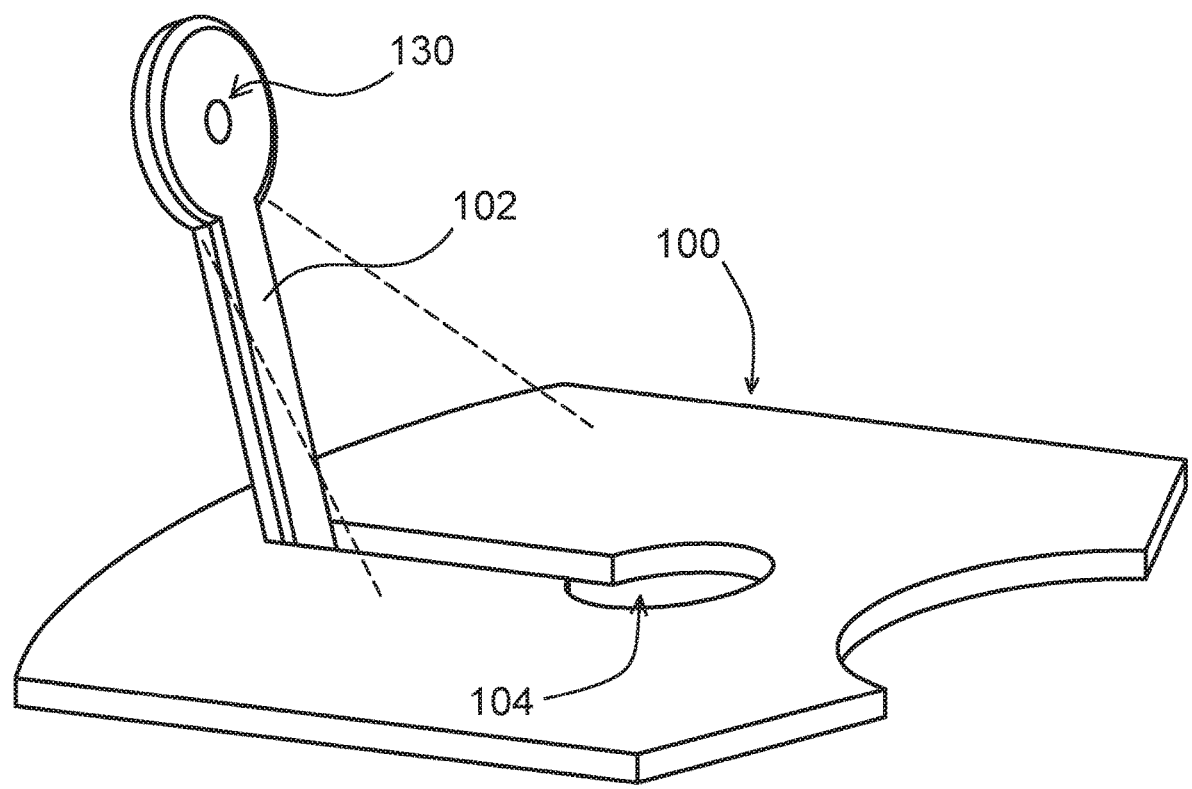
FIG. 4 is a perspective view of a third exemplary embodiment of a scanning device according to the present disclosure.

In various exemplary embodiments, one or more of the sensors, or reflecting mirrors, are designed to be in one of two discreet states: one in which they are stored within the profile of the foot platform and a second in which they are in a deployed state where they are in an appropriate position and angle for full viewing and sensing of the foot, ankle, and/or lower leg. Such embodiments are shown in FIGS. 2, 3, and 4. In these embodiments, the sensor arrays are located on pivoting structures 102 that are movable into and out of apertures 104 in the platform 100. This is advantageous for improving safety for users and reducing the risk of damage to the imaging sensors.

In various exemplary embodiments, the one or more imaging sensors include one or more longwave infrared (LWIR) imaging cameras or thermal cameras. These cameras detect heat differences across the feet that can be indicative of a wide variety of health and wellness issues.

In various exemplary embodiments, the one or more imaging sensors include one or more near infrared (NIR) sensitive cameras and a source of NIR light. By illuminating the veins with NIR light, veins located just below the skin can be detected, evaluated, and tracked. Data gathered over time about veins allows one to track trends and detect changes in size and other characteristics, including varicose veins. This information may be used to monitor indicators for potential blood clots, blood flow, and general vein health.

In various embodiments, the one or more imaging sensors include one or more visual light cameras. Computer vision may be used to process and analyze the images for indicators of many different health and wellness issues. Current images may also be compared to past images to identify changes and indicators of health and wellness issues.

In various exemplary embodiments, the one or more imaging sensors include one or more 3D cameras. 3D cameras are used to gather spatial information and data about the size and shape of the feet. This data can be used to track changes in the size and dimension of the feet indicative of health and wellness problems such as, but not limited to, swelling, water retention, blood circulation deficiencies, bunions, growths, hammer toes and other toe deformities, and arch problems.

In various exemplary embodiments, the one or more imaging sensors include one or more ultrasonic 3D imaging devices. Ultrasound technology may be used to create images of the inside of the foot.

In various exemplary embodiments, the one or more imaging sensors include one or more infrared (IR) cameras. Temperature data can be used to identify hot spots indicative of injury or developing conditions before they manifest noticeable symptoms. It can also be used to monitor general blood flow through the feet and other health and wellness indicators.

In various exemplary embodiments, the one or more sensors may comprise an array of sensors including one or more, including all possible combinations, of the sensors described above.

Referring to FIG. 2, a first exemplary embodiment of a scanning device is shown. In this embodiment, two imaging sensor arrays 110 are shown. The arrays 110 are designed to move between an active position protruding up from a platform 100 and an inactive position (not shown) fitted into the platform 100. In this embodiment, the two sensor arrays 110 are located proximate to an edge of the platform 100 disposed toward opposite sides of the platform 100. The imaging sensors in the arrays 110 are positioned with one in front and above each foot. In various other exemplary embodiments, sensor arrays 110 may be placed on or more other sides or in the interior of the platform 100.

Referring to FIG. 3, a second exemplary embodiment of a scanning device is shown. In this embodiment, two imaging sensor arrays 120 are shown. The arrays 120 are designed to move between an active position protruding up from a platform 100 and an inactive position (not shown) fitted into the platform 100. In this embodiment, the two sensor arrays 120 are located at each of the front corners of the platform 100. The imaging sensors in the arrays 120 are positioned above, in front, and to the sides of the user's feet. In various other exemplary embodiments, sensor arrays 120 may be placed on or more other sides or in the interior of the platform 100.

Referring to FIG. 4, a third exemplary embodiment of a scanning device is shown. In this embodiment, one imaging sensor array 130 is shown. The array 130 is designed to move between an active position protruding up from a platform 100 and an inactive position (not shown) fitted into the platform 100. In this embodiment, the sensor array 130 is located toward the front edge of the platform 100 and between the user's feet. The imaging sensors in the sensor array 130 are adapted to view both feet. In various other exemplary embodiments, sensor arrays 130 may be placed on or more other sides or in the interior of the platform 100.

Figure 5:
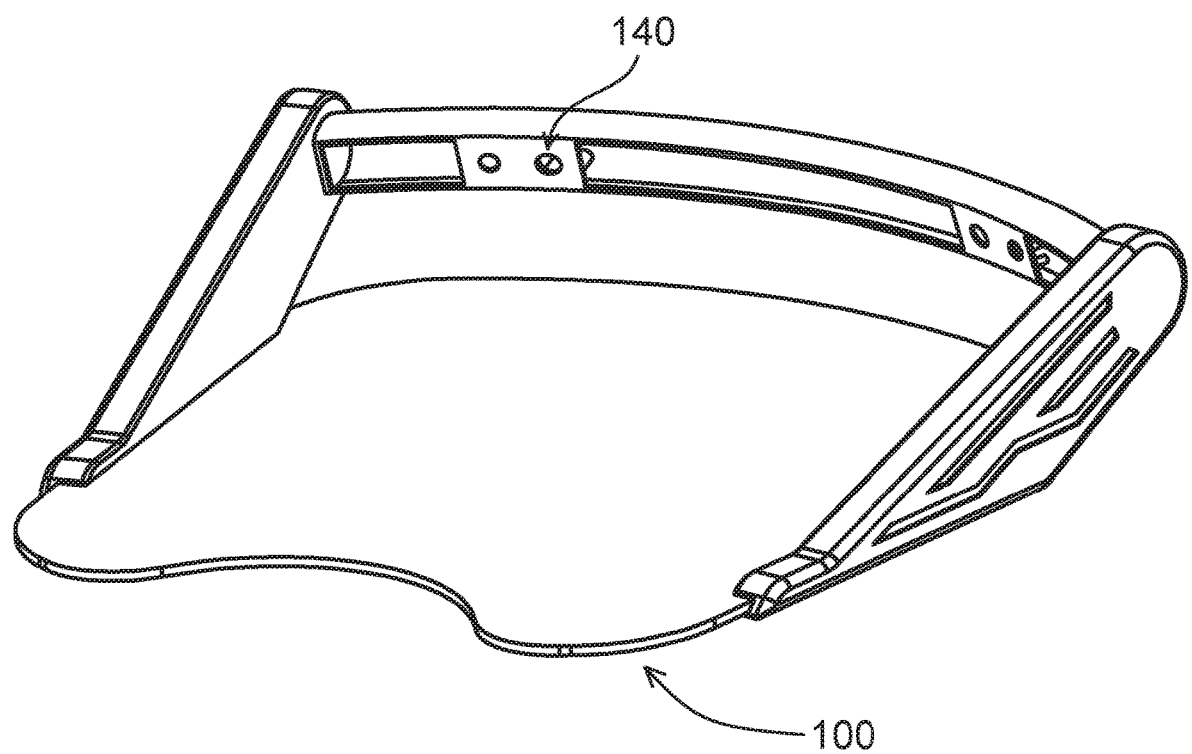
FIG. 5 is a perspective view of a fourth exemplary embodiment of a scanning device according to the present disclosure.

Referring to FIG. 5, a fourth exemplary embodiment of a scanning device is shown. In this embodiment, one imaging sensor array 140 is shown. The array 140 is positioned in a horizontal bar above the user's feet and extending across substantially all the width of the platform 100. In various other exemplary embodiments, sensor arrays 140 may be placed on or more other sides or in the interior of the platform 100. In still other exemplary embodiments, the array is adapted to raise to get a better angle on the user's feet when placed on the platform and lower when the appropriate images have been captured.

Figure 6:
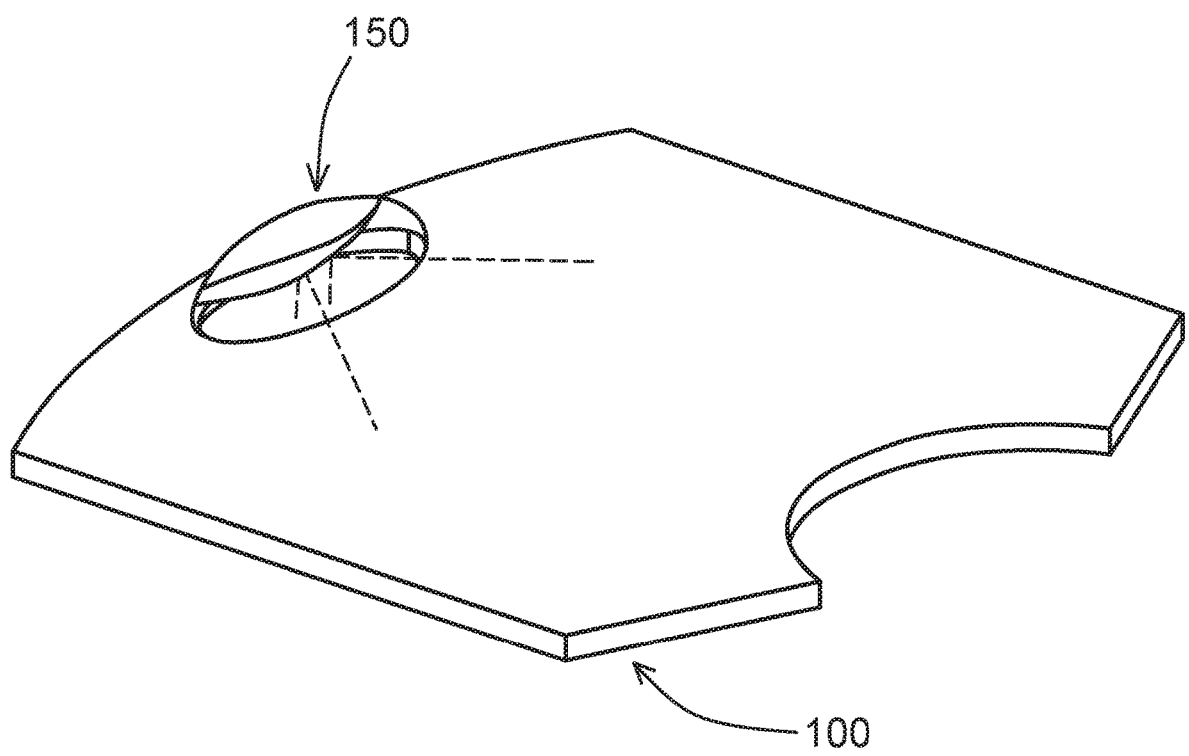
FIG. 6 is a perspective view of a fifth exemplary embodiment of a scanning device according to the present disclosure.

Referring to FIG. 6, a fifth exemplary embodiment of a scanning device is shown. In this embodiment, one imaging sensor array 150 is shown. The sensor array 150 is in an oval dome located at the front center of the platform 100. In various other exemplary embodiments, sensor arrays 150 may be placed on or more other sides or in the interior of the platform 100.

Figure 7:
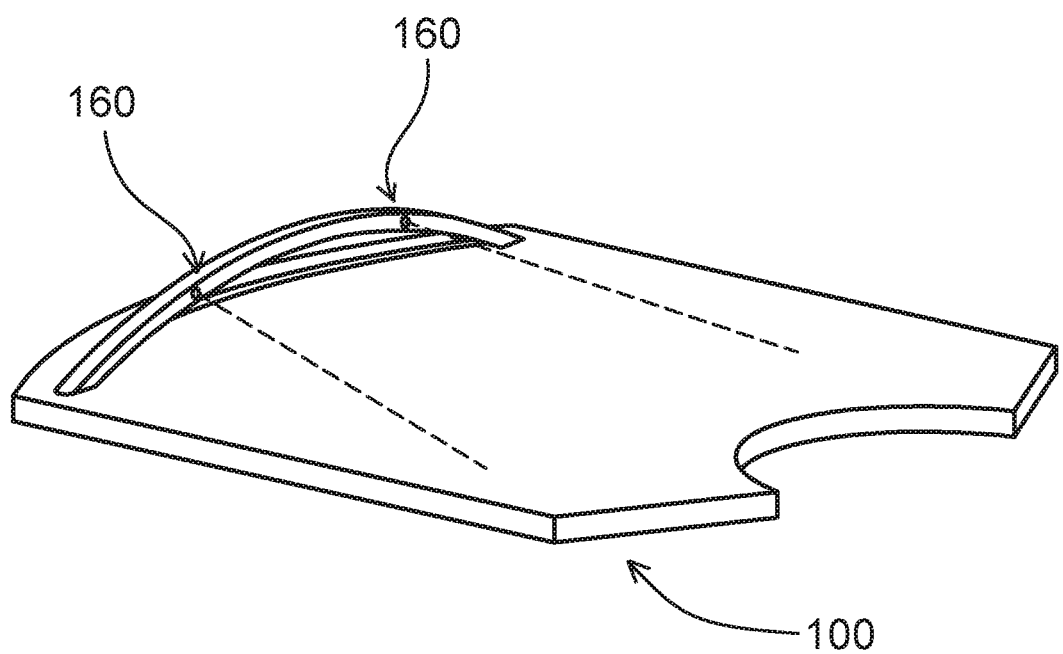
FIG. 7 is a perspective view of a sixth exemplary embodiment of a scanning device according to the present disclosure.

Referring to FIG. 7, a sixth exemplary embodiment of a scanning device is shown. In this embodiment, one imaging sensor array 160 is shown. The sensor array 160 is positioned in an arch extending across the front edge of the platform 100. In various other exemplary embodiments, sensor arrays 160 may be placed on or more other sides or in the interior of the platform 100.

Figure 8:
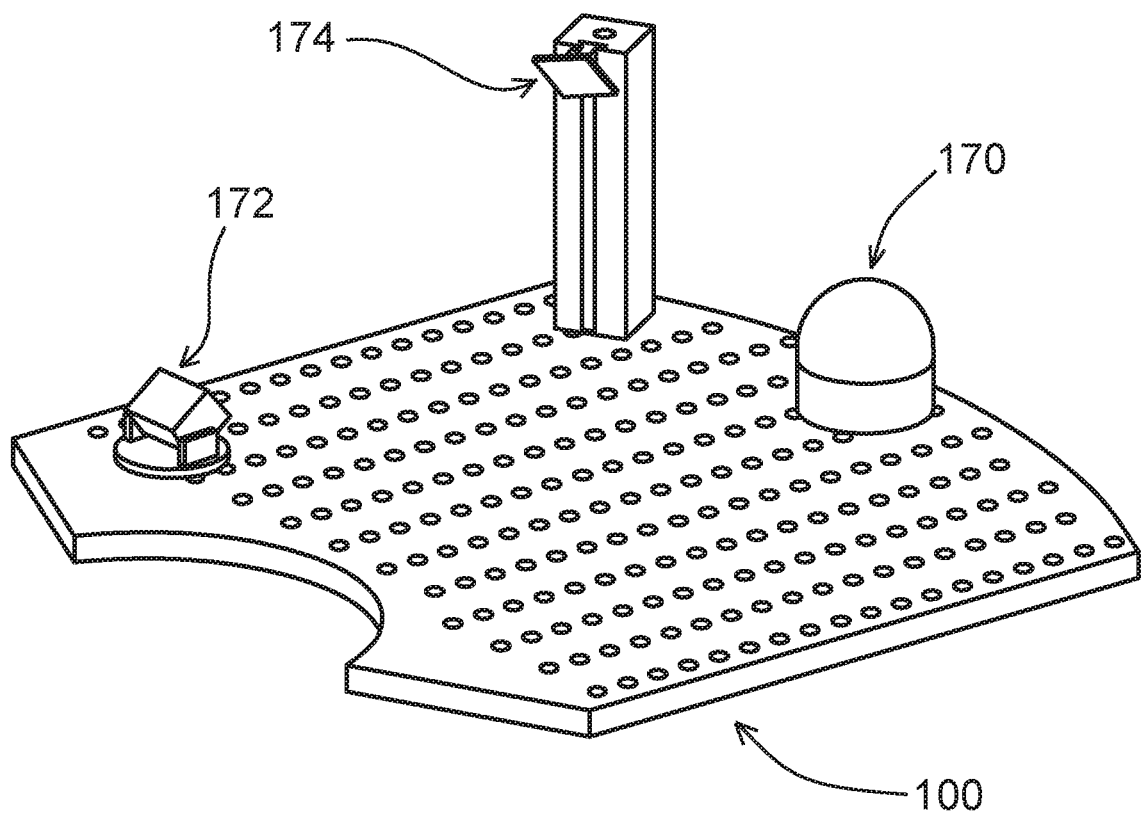
FIG. 8 is a perspective view of a seventh exemplary embodiment of a scanning device according to the present disclosure.

Referring to FIG. 8, a seventh exemplary embodiment of a scanning device is shown. In this embodiment, an imaging sensor array 170 is located at the front center of the platform

100. An emitter 172 emits light (e.g., NIR light) toward a reflecting mirror 174 that redirect that light onto the user's feet. In various other exemplary embodiments, sensor arrays 170, emitter 172, and reflecting mirror 174 may be placed on or more other sides or in the interior of the platform 100.

Figure 9:
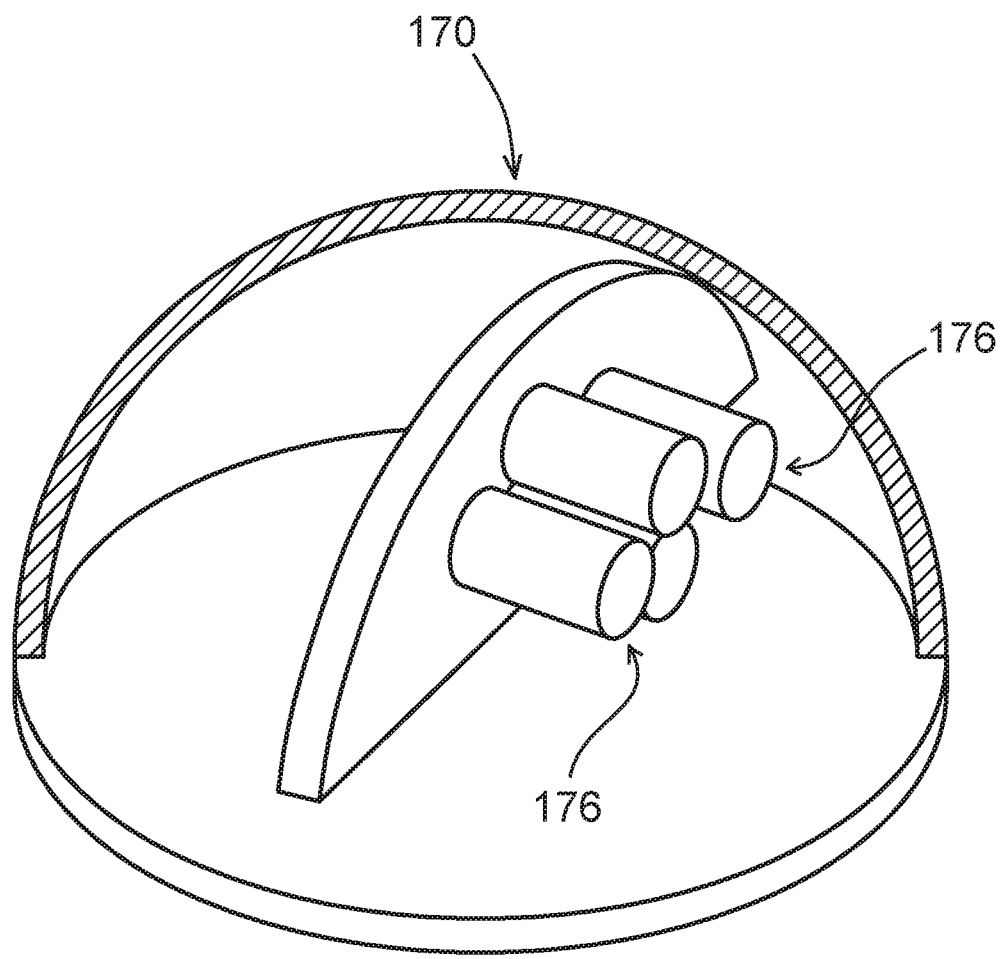
FIG. 9 is a partial cross-section perspective view of a scanning array according to the present disclosure.

Referring to FIG. 9, scanner array 170 is shown in greater detail by way of example. The imaging sensor array 170 includes multiple sensors 176 of various types as described above. As with imaging sensor array 170, all the imaging sensor arrays described herein are adapted to include one or more sensors of one or more types. In various exemplary embodiments, including all of those specifically discussed herein, the sensor arrays may include all or any combination of the types of sensors discussed herein and other sensors.

Figure 10:
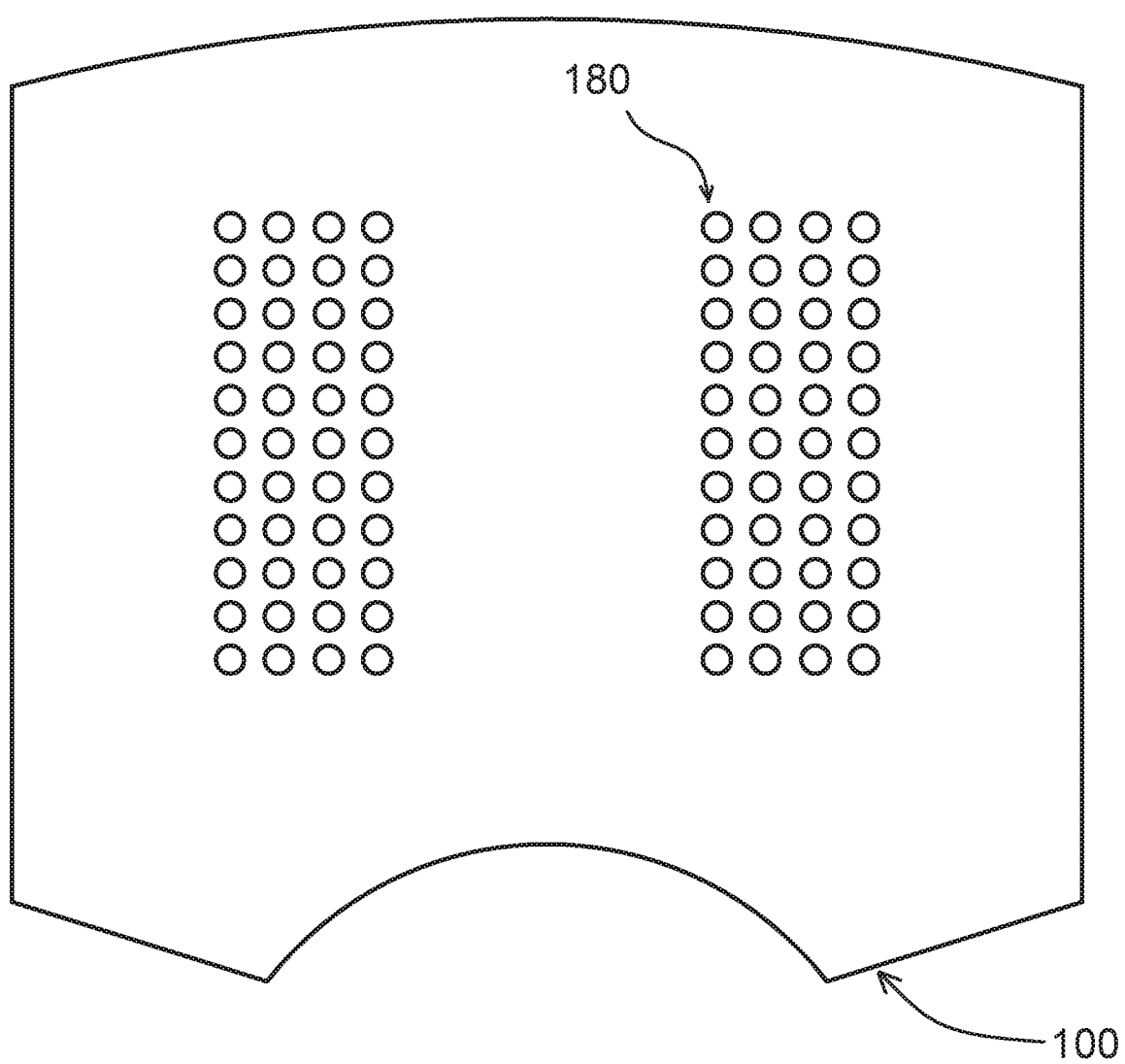
FIG. 10 is a top plan view of an eighth exemplary embodiment of a scanning device according to the present disclosure.

Referring to FIG. 10, an eighth exemplary embodiment of a scanning device is shown. In this embodiment, at least one scanner array 180 is positioned under the platform 100. In this embodiment, the imaging sensor array 180 may include multiple single point infrared thermal sensors to create a thermal image of the foot as well as other sensor types. The resolution of the thermal image depends on the number and placement of sensors. In this embodiment, at least a portion of the platform 100 is transparent to the imaging scanners in the array 180. The data from the single point infrared thermal sensors in the sensor array 180 are assembled to form an image of the bottom of the user's feet.

Figure 11:
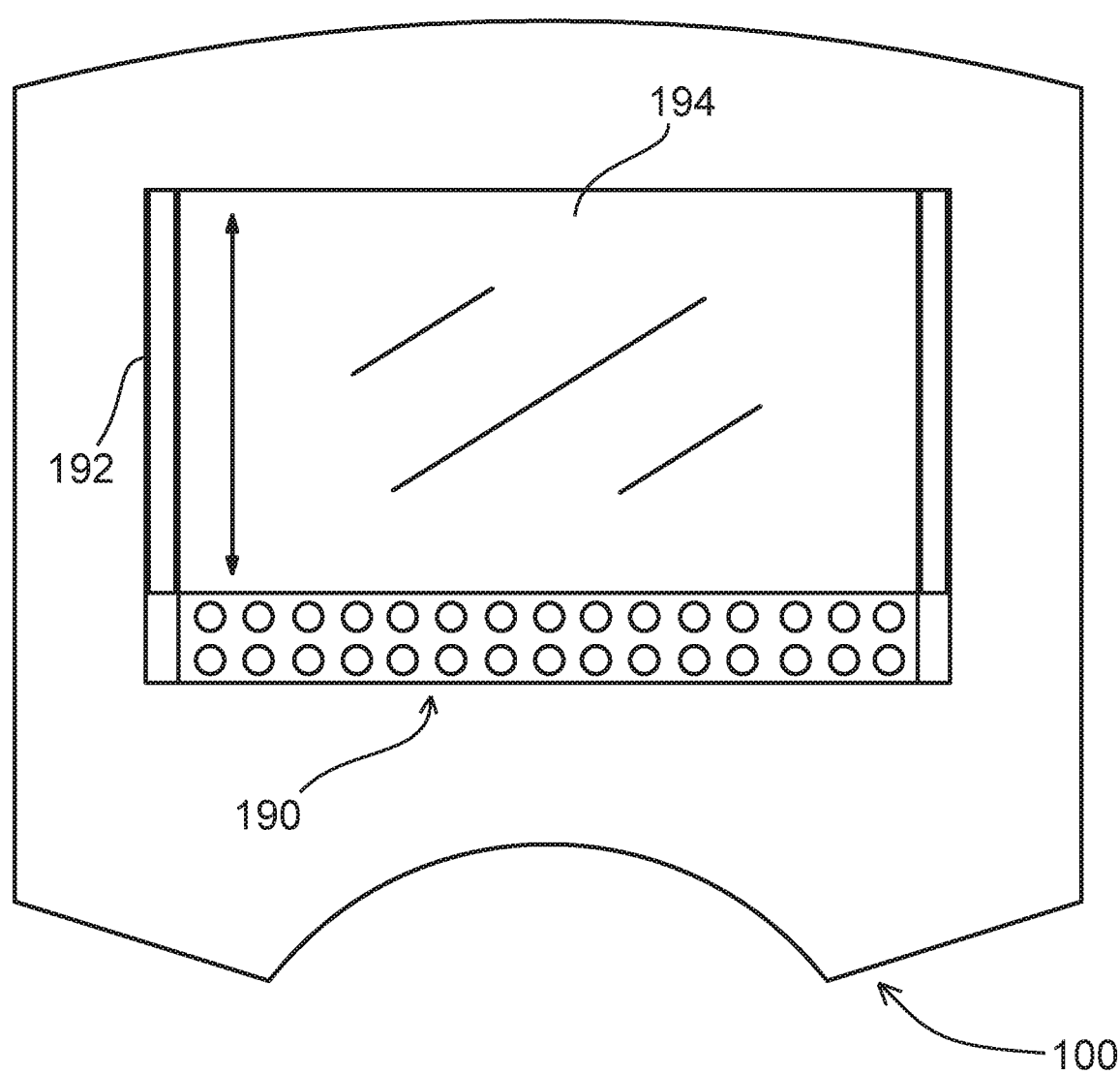
FIG. 11 is a top plan view of a ninth exemplary embodiment of a scanning device according to the present disclosure.

Referring to FIG. 11, a ninth exemplary embodiment of a scanning device is shown. In this embodiment, at least one imaging sensor array 190 is arranged in a line and placed under the user's feet. In various exemplary embodiments, scanner array 190 is moved from front-to-back, or vice versa, via tracks 192 or any other appropriate mechanism. The scanner array 190 may also be positioned for left-to-right, or vice versa, movement for scanning and imaging. In various exemplary embodiments, the scanner array 190 is placed under a window of transparent material to facilitate scanning.

Figure 12:
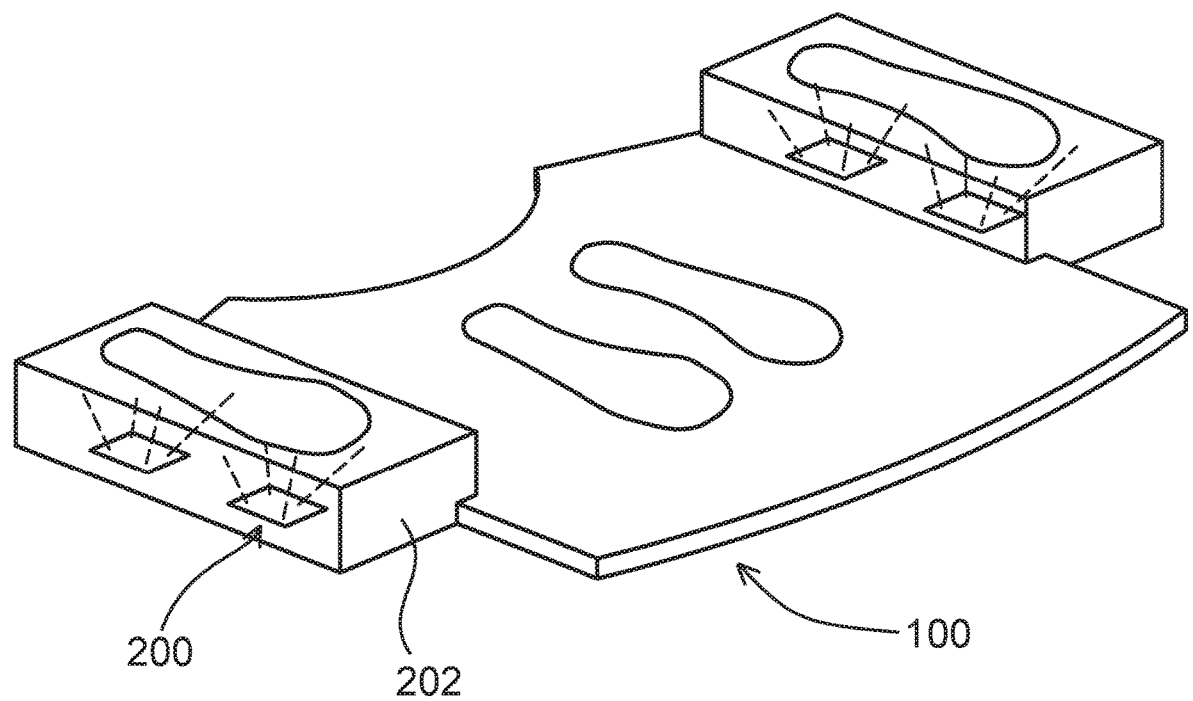
FIG. 12 is a perspective view of a tenth exemplary embodiment of a scanning device according to the present disclosure.

Referring to FIG. 12, a tenth exemplary embodiment of a scanning device is shown. In this embodiment, two raised platforms 202 are located to either side of platform 100. Each raised platform 102 contains at least one scanner array 200.

Figure 13:
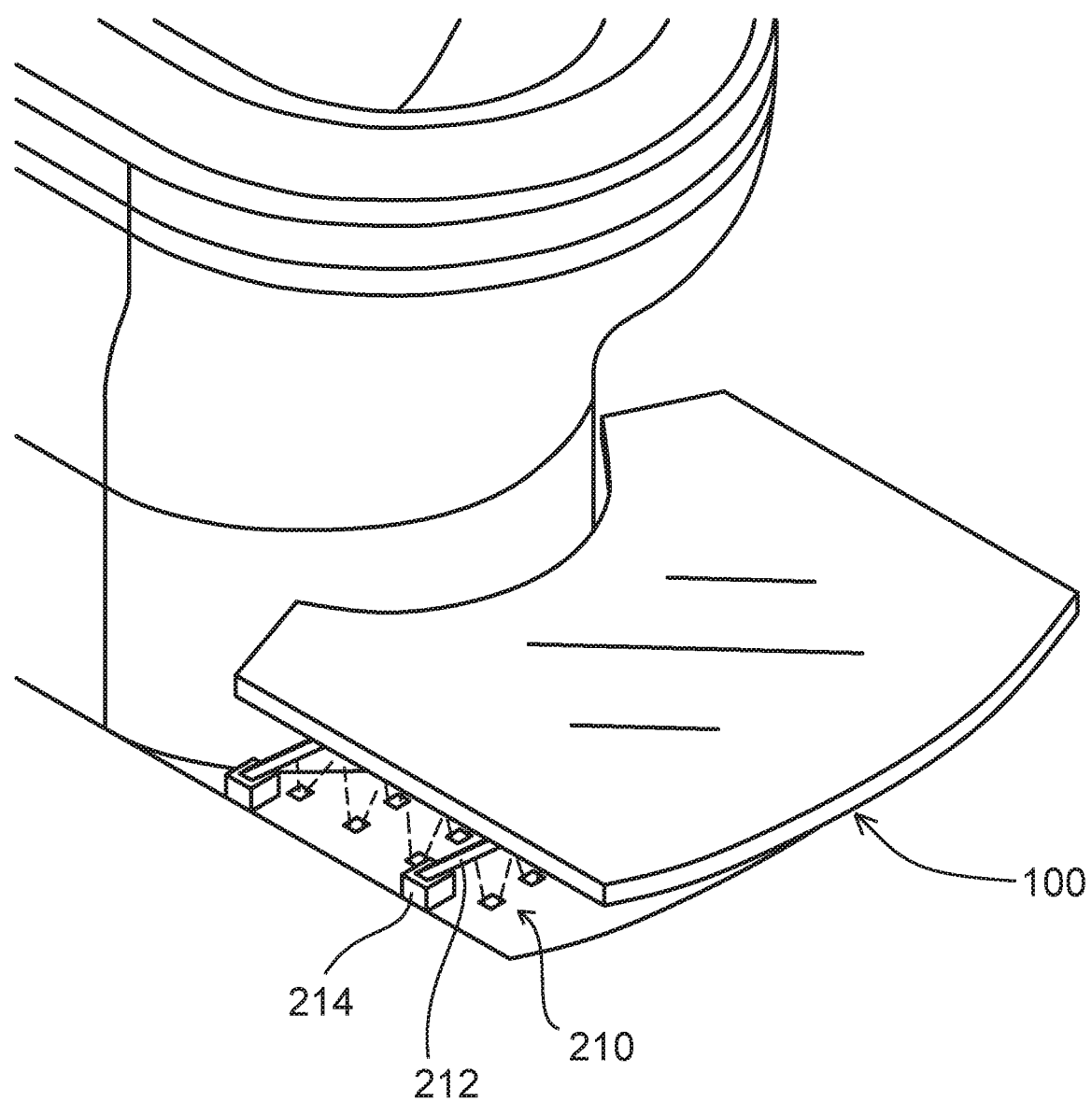
FIG. 13 is a is perspective view of an eleventh exemplary embodiment of a scanning device according to the present disclosure.

Referring to FIG. 13, an eleventh exemplary embodiment of a scanning device is shown. In this embodiment, the at least one imaging sensor array 210 is positioned under the user's feet. The platform 100 is connected to and supported by a plurality of arms 212. The arms 212 are connected to actuators 214 that move the arms to lift and lower the platform 100 between a raised position and a lowered position. In this embodiment, the raised position is a preferred position for scanning the bottom of the user's feet. In various exemplary embodiments, platform 100 is preferably made from a transparent material.

Figure 14:
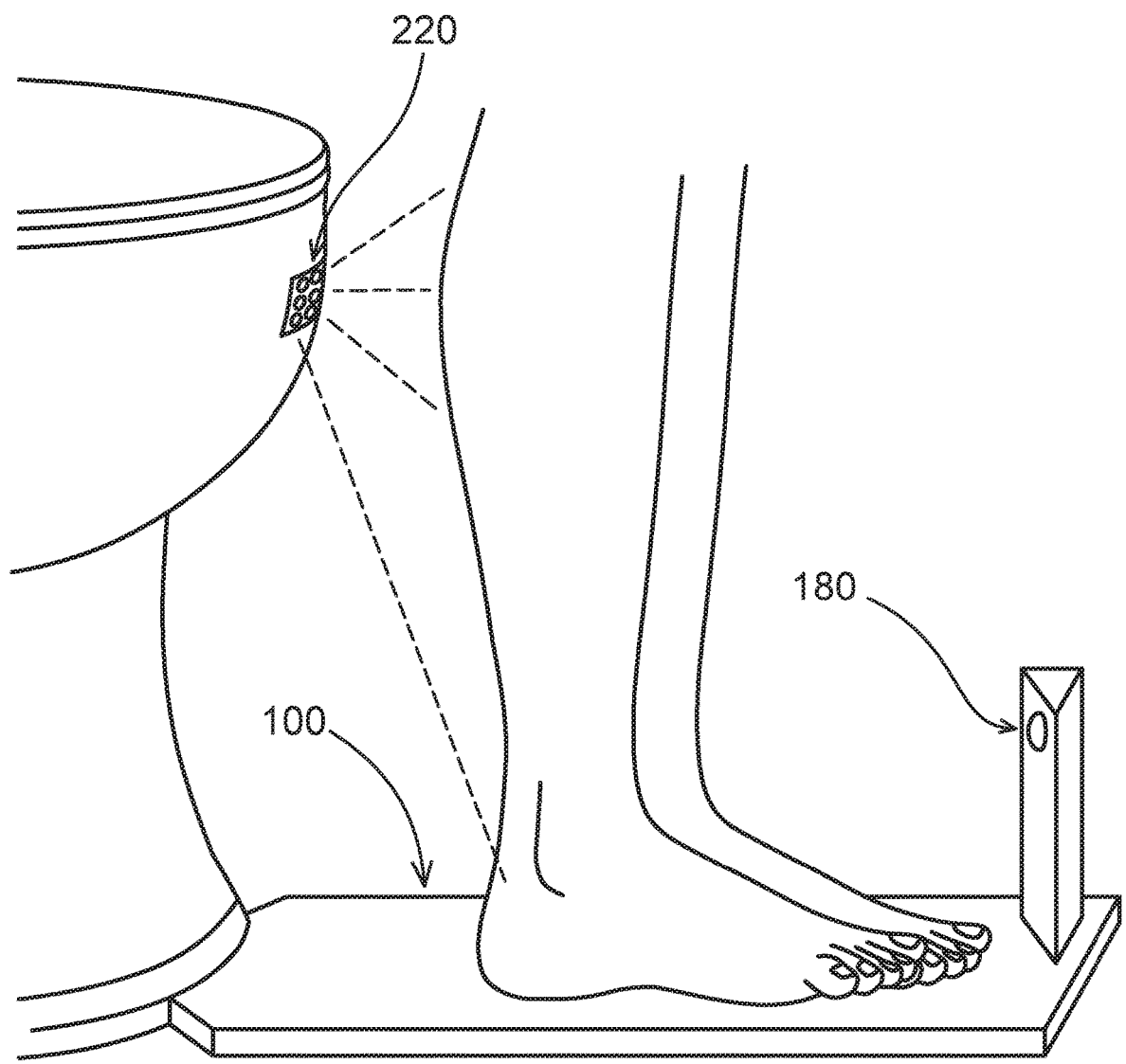
FIG. 14 is a perspective view of a twelfth exemplary embodiment of a scanning device according to the present disclosure.

Referring to FIG. 14, a twelfth exemplary embodiment of a scanning device is shown. In this embodiment, at least one imaging sensor array 190 is attached to or positioned in a smart toilet such that the backs of the feet, ankle, and leg may be imaged; at least one scanner array (not shown in FIG. 14) is located under the platform 100; and at least one array 220 is positioned to the front of the platform 100. In this and similar embodiments, multiple arrays of one or more types are positioned to provide complete imaging of the entire foot. Sensor array 190 is particularly well adapted to monitor the condition of the legs by looking at blood flow, vein condition, swelling, protrusions, potential blood clots, and skin texture among others.

Figure 15:
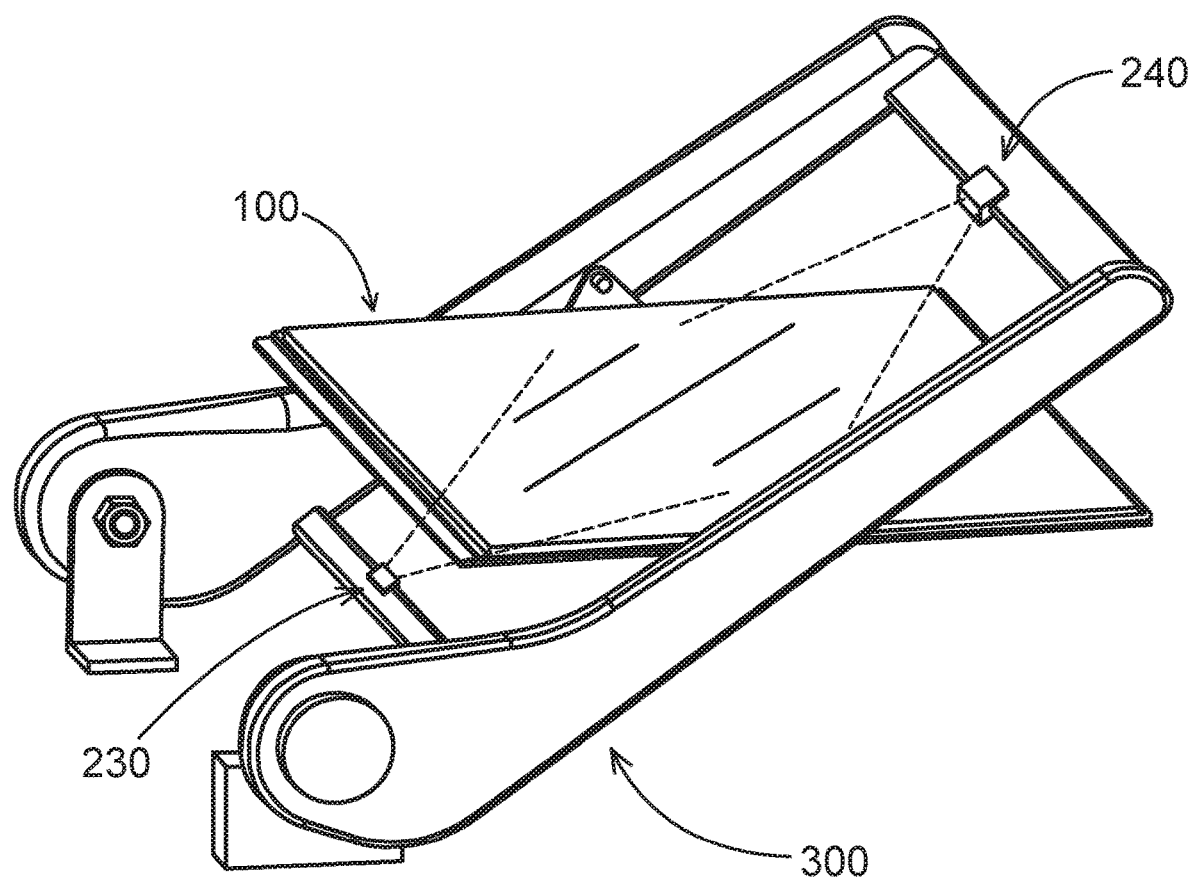
FIG. 15 is a perspective view of a thirteenth exemplary embodiment of a scanning device.

Referring to FIG. 15, a thirteenth exemplary embodiment of a scanning device is shown. In this embodiment, at least one imaging sensor array 230 is positioned below the user's feet and another imaging sensor array 240 is positioned above the user's feet. The platform 100 is supported by a frame 300 that may be raised as shown to a position that places the user's feet in a good position for imaging. When not in use, the platform is preferably lowered to floor level.

In various exemplary embodiments, the various sensor arrays may be fixed or may be adapted to move to obtain more complete and accurate images. For example, sensor array 190 in FIG. 14 may be designed to move up and down during scanning.

In various exemplary embodiments, the system may include one or more of the imaging sensor arrays described above located at various positions to the front, back, sides, above, below, or in between a user's feet in order to create complete images of the user's feet, ankles, and lower legs. The sensors are positioned so as to enable them to create one or more images that together cover all or substantially all of the user's feet.

In an exemplary embodiment, the system includes at least one processor that received data from the one or more imaging sensors. The processor(s) is adapted to process data from the one or more imaging sensors to create one or more images. The processor(s) is also adapted to analyze the one or more images to detect anomalies and potential problems. The processor(s) is also adapted to compare the one or more images processed currently with past images of the same user to detect changes over time.

In various exemplary embodiments, the processor(s) may be located in the same structures as the platform, associated hardware, and/or remotely. The same processor may perform multiple tasks for the system. Alternatively, different processors may be used for separate tasks performed by the system. In various exemplary embodiments of a smart toilet or smart scale, the processor may analyze additional health and wellness data gathered by other parts of the smart system such as sensors or other apparatus for isolating, examining, and analyzing excreta. Testing of excreta is common in medical labs for a variety of purposes and may be automated in a smart toilet system.

In an exemplary embodiment, the system makes data gathered and processed available to the user via one or more channels, e.g. via a digital device. In a preferred embodiment, the digital device is a smart phone. In other exemplary embodiments, digital device is a computer, tablet, or other electronic device. Preferably, the system provides a report to each user of the system. In addition, a report may be provided to a healthcare provider, a care giver or a family member. Preferably, the report is prepared in such a way as to provide useful and easily understood information. Also, the report preferably includes information on trends, i.e. to indicate if conditions have gotten worse or better over time.

In all embodiments, the system is designed so that the imaging scanners are focused on the platform area and the user's feet such that the scanning cameras do not record any other parts of the user's body. In various embodiments, additional security measures such as cryptography and image obfuscation may be used to protect the user's privacy, identity, and personal information.

In various exemplary embodiments, artificial intelligence may be used to examine and analyze the data from any or all of the imaging sensors discussed herein using algorithms such as those used in computer vision and other relevant processing methods.

In various exemplary embodiments, the user may provide feedback about the accuracy or usefulness of the data provided. As such feedback is provided, the computer vision system will learn more about feet and become more accurate in identifying health and wellness issue indicators, possibly including previously unknown indicators. The system may also be trained to identify additional indicators that are discovered over time.

All patents, published patent applications, and other publications referred to herein are incorporated herein by reference. The invention has been described with reference to various specific and preferred embodiments and techniques. Nevertheless, it is understood that many variations and modifications may be made while remaining within the spirit and scope of the invention.

What is claimed is:

1. A system to provide health and wellness data to a user, comprising:
   a platform for placement of a user's feet;
   at least one imaging sensor associated with the platform for capturing images of the user's feet; and
   a processor adapted to analyze the images to determine health and wellness data provided to the user;
   wherein the at least one imaging sensor is positioned in or on a base of a toilet.

2. The system of claim 1, wherein the at least one imaging sensor comprises an array of sensors comprising at least one of an infrared imaging sensor, a near infrared imaging sensor, a visual camera, a 3D camera, and an ultrasonic 3D imaging sensor.

3. The system of claim 1, wherein the at least one imaging sensor is positioned in at least one of below, above, between, in front of, to a side of, or behind the user's feet.

4. The system of claim 1 wherein the device is configured to capture at least one image of the front of the user's feet as the user faces the toilet and at least one image of the back of the user's feet as the user sits on the toilet.

5. The system of claim 1, wherein the health and wellness data are determined by comparing images captured on different days to detect changes over time.

6. The system of claim 1, wherein the platform is also configured to determine weight of the user.

7. A toilet for assessing health and wellness of a user, comprising:
   a bowl supported by a base;
   a platform for placement of a user's feet;
   at least one imaging sensor mounted in or on the base for capturing images of the user's feet; and
   a processor adapted to analyze the images to determine health and wellness data for the user.

8. The toilet of claim 7 further comprising one or more additional imaging sensors mounted on the platform for capturing images of the user's feet.

9. The toilet of claim 8, wherein the at least one imaging sensor and one or more additional imaging sensors are adapted to capture at least one image of the user's feet as the user faces the toilet and at least one image of the user's feet as the user sits on the toilet.

10. The toilet of claim 8, wherein the at least one imaging sensor and one or more additional imaging sensors comprise one or more arrays of sensors comprising at least one of an infrared imaging sensor, a near infrared imaging sensor, a visual camera, a 3D camera, and an ultrasonic 3D imaging sensor.

11. The toilet of claim 8, wherein the at least one imaging sensor and one or more additional imaging sensors are located in one or more positions below, above, in front, behind, or to a side of a user's feet.

12. The toilet of claim 7, further comprising sensors for assessing properties of excreta and wherein the processor is further adapted to analyze the properties in determining health and wellness data for the user.

13. The toilet of claim 8 wherein the at least one imaging sensor and one or more additional imaging sensors comprises one or more of an infrared imaging sensor, a near infrared imaging sensor, a visual camera, and a 3D camera.

14. The toilet of claim 8 wherein the at least one imaging sensor and one or more additional imaging sensors are positioned at one or more of below, above, between, behind, to the side, or to a side of the user's feet.

15. A method for assessing health and wellness comprising:
   acquiring one or more images of the foot of a user using one or more imaging sensors;
   using a processor to analyze the one or more images for health and wellness factors; and
   making the results of the health and wellness analysis available to the user on one or more digital platforms;
   wherein the one or more imaging sensors are located in or on a base of a toilet.

16. The method of claim 15, wherein the images are acquired using one or more imaging sensors comprising at least one of an infrared thermal imaging sensor, a near infrared thermal imaging sensor, a visual light imaging sensor, a 3D imaging sensor, or an ultrasonic 3D imaging sensor.

17. The method of claim 15, wherein the one or more imaging sensors are located at one or more of below, above, behind, between, in front of, or to the side of the user's feet.

18. The method of claim 15, wherein the results of the health and wellness analysis are determined by comparing images captured on different days to detect changes over time.

* * * * *